United States Patent [19]

Peters

[11] Plant 5,074

[45] Jul. 26, 1983

[54] PLUM TREE (AP-3)

[76] Inventor: Alvin Peters, 41736 Road 62, Reedley, Calif. 93654

[21] Appl. No.: 340,454

[22] Filed: Jan. 18, 1982

[51] Int. Cl.[3] ..... A01H 5/03
[52] U.S. Cl. ..... Plt./38
[58] Field of Search ..... Plt./38

*Primary Examiner*—Robert E. Bagwill
*Attorney, Agent, or Firm*—Roger B. Webster

[57] ABSTRACT

A plum tree which is large, vigorous, semi-spreading, dense, vase-formed, and hardy; foliated with medium size, oblanceolate, acutely pointed leaves having a coarsely serrate margin, and medium size, opposite, green, globose glands; blooms from large, hardy, plump buds; the flowers, of medium season, being of medium size and white; and is a regular and productive bearer of medium size, uniform, symmetrical, globose, late-ripening, clingstone fruit having orange-yellow skin substantially overspread with red, and yellow flesh.

1 Drawing Figure

BACKGROUND OF THE VARIETY

1. Field of the Invention

In the course of the maintenance of a Laroda plum orchard on my ranch located near Dinuba, Turlare County, Calif., I frequent such orchard for the purpose of inspection, cultivation, and irrigation, and — during the course of such activities — I am aware of the condition of the trees and recognize any other-than-normal growth characteristics of them. It was under such conditions that the present variety of plum tree was discovered by me.

2. Classification of the Variety

The present variety of plum tree is embraced by Class 38, Plants, of the United States Patent Office Manual of Classification.

3. Prior Varieties

Among existing varieties of plum trees which are known to me, and mentioned herein, is the Laroda (unpatented).

ORIGIN OF THE VARIETY

The present variety of plum tree was discovered by me as a bud sport limb on a Laroda plum tree in the aforesaid orchard on my ranch located near Dinuba, Tulare County, Calif.; it having been recognized by me that the fruit on such bud sport limb ripened substantially later than the fruit on other limbs of said tree. Such bud sport limb was maintained, by me, under careful and continuing observation, and — upon further confirmation of the late-ripening characteristic of its fruit, and because of its potential commercial value — I determined to effect asexual reproduction of the variety represented by said bud sport limb.

ASEXUAL REPRODUCTION OF THE VARIETY

Asexual reproduction of the variety was successfully accomplished, by me, in an orchard on my ranch located near Reedley, Fresno County, Calif., by grafting scion wood on both plum and nectarine trees; such asexual reproductions, in maturity, having run true to the original tree in all respects.

SUMMARY OF THE VARIETY

The present variety of plum tree is large, vigorous, semi-spreading, dense, vase-formed, and hardy; foliated with medium size, oblanceolate, acutely pointed leaves having a coarsely serrate margin, and medium size, opposite, green, globose glands; blooms from large, hardy, plump buds; the flowers, of medium season, being of medium size and white; and is a regular and productive bearer of medium size, uniform, symmetrical, globose, late-ripening, clingstone fruit having orange-yellow skin substantially overspread with red, and yellow flesh.

The present variety of plum tree — while otherwise most similar to the Laroda in tree and fruit characteristics — is novel and distinctive in that such tree bears fruit which ripens about six to seven weeks later than the fruit of the Laroda.

BRIEF DESCRIPTION OF THE DRAWING

The drawing is an illustration, by photographic reproduction in color, of one of the fruit shown with leaves, and other separate fruit; one of the latter being half cut away to expose the flesh and stone.

DESCRIPTION OF THE VARIETY

The botanical details of this new and distinct variety of plum tree — with color definitions (except those in common color terms) referenced to Maerz and Paul Dictionary of Color (1950 edition) — are as follows:

Tree:
- *Size.*—Large.
- *Vigor.*—Vigorous.
- *Growth.*—Semi-spreading.
- *Density.*—Dense.
- *Form.*—Vase-formed.
- *Hardiness.*—Hardy.
- *Production.*—Productive.
- *Bearing.*—Regular bearer.

Trunk:
- *Size.*—Stocky.
- *Texture.*—Medium.

Branches:
- *Size.*—Stocky.
- *Texture.*—Medium.
- *Color.*—Dull gray (8-C-9). Color in cracks — India tan (7-C-12).
- *Lenticels.*—Number — Numerous. Size — Small.

Leaves:
- *Size.*—Medium. Length range — 75–82 mm. Width range — 31–34 mm.

*Form.*—Oblanceolate. Acutely pointed.
*Thickness.*—Medium.
*Texture.*—Smooth.
*Margin.*—Coarsely serrate.
*Petiole.*—Long — Range (variable) 10–24 mm. Medium thickness (1.2 mm.).
*Glands.*—Average number — 2. Opposite. Medium size. Globose. Green.
*Stipules.*—Wanting.
*Color.*—Top side — Medium green (23-H-5). Under side — Lighter green (23-J-2).

Flower buds:
*Hardiness.*—Hardy.
*Size.*—Large.
*Length.*—Medium.
*Form.*—Plump.

Flowers:
*Blooming period.*—Date of first bloom — Feb. 16, 1981. Date of full bloom — Feb. 23, 1981. Medium, as compared with other varieties. Size — Medium. Color — White.

Fruit:
*Maturity when described.*—Eating ripe — Sept. 10, 1981.
*Date of first picking.*—Aug. 25, 1981.
*Date of last picking.*—Sept. 5, 1981.
*Size.*—Uniform. Medium. Average diameter axially — 58 mm. Average transversely in suture plane — 56 mm. Average at right angles to suture plane — 54 mm.
*Form.*—Uniform. Symmetrical. Globose.
*Suture.*—An inconspicuous line.
*Ventral surface.*—Rounded slightly.
*Cavity.*—Abrupt. Elongated in suture plane, with suture showing on one side. Depth — 8–10 mm. Breadth — 10 mm.
*Base.*—Truncate.
*Apex.*—Rounded to truncate.
*Pistil point.*—Wanting.

Skin:
*Thickness.*—Medium.
*Texture.*—Medium.
*Tendency to crack.*—None.
*Color.*—Ground color — Orange-yellow (11-I-8). Blush color — Red (7-L-8).
*Bloom.*—Moderate.

Flesh:
*Amygdalin.*—Scant.
*Texture.*—Medium. Meaty.
*Fibers.*—Fine.
*Ripens.*—Evenly.
*Flavor.*—Subacid.
*Aroma.*—Wanting.
*Eating quality.*—Good.
*Color.*—Yellow (11-H-7). Surface of pit cavity — Yellow, with some brown mottling.

Stone:
*Type.*—Cling. Adheres to flesh over entire surface.
*Fibers.*—Short. Retains short fiber-like threads throughout.
*Size.*—Medium. Length range — 25–27 mm. Breadth range — 16–18 mm. Thickness range — 7–8 mm.
*Form.*—Oblong. Cuneate toward base and apex.
*Base.*—Straight.
*Hilum.*—Narrow. Oval.
*Apex.*—Acuminate.
*Sides.*—Unequal.
*Surface.*—Irregularly ridged throughout.
*Ridges.*—Jagged.
*Ventral edge.*—Thin, with wing near mid-point.
*Dorsal edge.*—Narrow. Shallow toward apex.
*Color.*—Tan (7-E-11).
*Tendency to split.*—Slight.

Use: Market; dessert.
Keeping quality: Good.
Resistance to insects and diseases: Good.
Shipping quality: Good.

The plum tree and its fruit herein described may vary in slight detail due to climatic and soil conditions under which the variety may be grown; the present description being of the variety as grown in the Central Valley of California.

I claim:

1. A new and distinct variety of plum tree, substantially as illustrated and described, which — while otherwise most similar to the Laroda in tree and fruit characteristics — bears fruit which ripens about six to seven weeks later than the fruit of the Laroda.

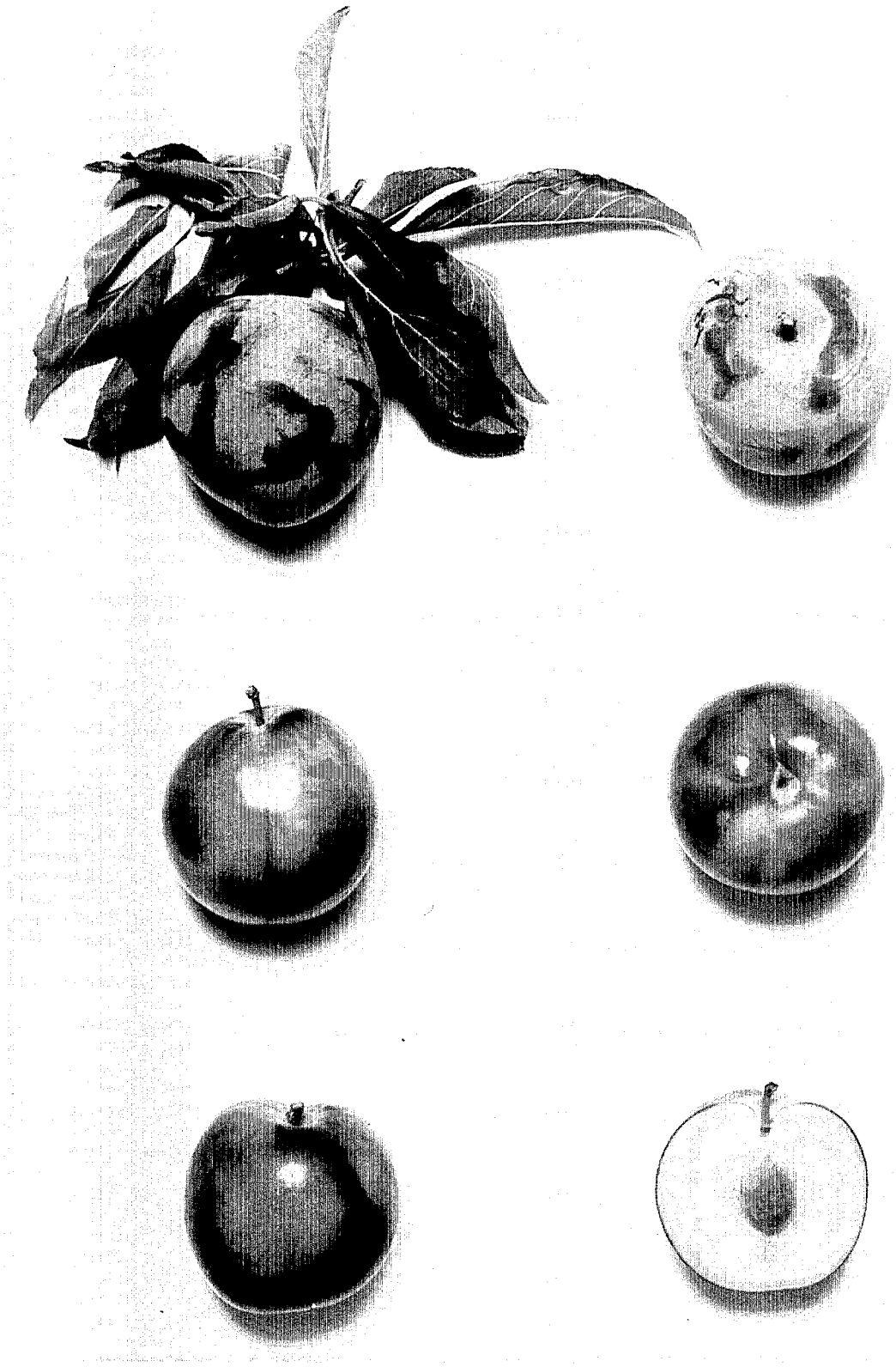

* * * * *